United States Patent

Kleiner

[11] 3,962,324
[45] June 8, 1976

[54] PROCESS FOR PREPARING HALOGENOMETHANE-PHOSPHONIC ACID DIHALIDES

[75] Inventor: Hans-Jerg Kleiner, Bad Soden, Taunus, Germany

[73] Assignee: Hoechst Aktiengesellschaft, Frankfurt am Main, Germany

[22] Filed: Dec. 3, 1973

[21] Appl. No.: 420,882

[30] Foreign Application Priority Data
Dec. 5, 1972  Germany............................ 2259454

[52] U.S. Cl. ............................................. 260/543 P
[51] Int. Cl.² ........................ C07F 9/38; C07F 9/42
[58] Field of Search................................. 260/543 P

[56] References Cited
UNITED STATES PATENTS 3,188,281  6/1965  Briggeman et al. ............. 260/543 P
3,200,145  8/1965  Lutz et al. ........................ 260/543 P FOREIGN PATENTS OR APPLICATIONS
2,129,584  12/1972  Germany......................... 260/543 P
2,132,962  1/1973  Germany......................... 260/543 P

*Primary Examiner*—Norman Morgenstern
*Attorney, Agent, or Firm*—Curtis, Morris & Safford

[57] ABSTRACT

Process for preparing halogenomethane-phosphonic acid dihalides of the formula

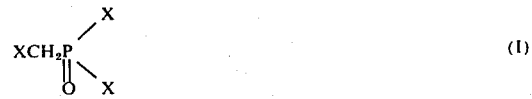

wherein X is halogen, preferably chlorine or bromine, by reacting hydroxymethane-phosphonic acids of the formula their salts or functional derivatives or thio-analogs, with acid halides of the formula

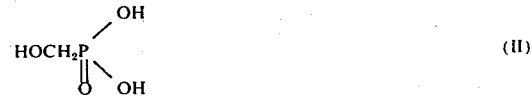

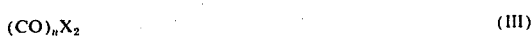

where $n$ is 1 or 2, in the presence of certain tri- or pentavalent nitrogen or phosphorus-containing compounds. The products are valuable intermediates for the preparation of pesticides and flame retardants.

2 Claims, No Drawings

PROCESS FOR PREPARING HALOGENOMETHANE-PHOSPHONIC ACID DIHALIDES

The present invention relates to a process for preparing halogenomethane-phosphonic acid dihalides.

It is already known that phosphorus trichloride and paraformaldehyde at temperatures of 250°C and under pressure react to yield chloromethane-phosphonic acid-dichloride. However, the yield is but 60–65 percent, no increase being possible (see Houben-Weyl, vol. 12/1 (1963), pg. 404.

The present invention provides a process for preparing halogenomethane-phosphonic acid dihalides having the general formula

(I)

wherein X is halogen, preferably chlorine or bromine, which comprises reacting hydroxymethanephosphonic acid having the formula

(II)

its salts or functional derivatives or the thio-analogs of said compounds, with acid halides having the formula

(III)

wherein $n$ is 1 or 2, in the presence of 1. compounds containing at least one 3- to 5-valent nitrogen or phosphorus atom, which is bound with at least 3 valencies to organic radicals having up to 20 carbon atoms, two of these valencies being able to form a double bond, or in presence of
2. fully amidated tribasic organic or inorganic acids of 3-valent or 5-valent phosphorus, the nitrogen-atoms of which are substituted by aliphatic radicals having up to 20 carbon atoms and the organic radicals of which may contain up to 20 carbon atoms, optionally in presence of an inert solvent.

Suitable salts of hydroxymethane-phosphonic acid are especially alkali metal and ammonium salts. Suitable functional derivatives are, for example, diesters, monoesters and their salts, pyrophosphonic acid ester, as well as the thio-analogs of these substances. Preferred initial materials are the free acid, the salts thereof and neutral esters, because of their relatively easy accessibility. The chemical nature of the ester group is not essential for the process though for practical reasons lower alkyl esters ($C_1$–$C_6$) are preferred.

In particular the following initial compounds may be considered for example:
hydroxymethane-phosphonic acid dimethyl ester, diethyl ester, dipropyl ester, di-n-butyl ester, diisobutyl ester, dioctyl ester, didodecyl ester, the corresponding semi-esters and their sodium salts, hydroxymethane-phosphonic acid and the monosodium salt or -disodium salt of hydroxymethane-phosphonic acid.

Said initial products are easily accessible according to known methods from phosphorous acid or its dialkyl esters, and paraformaldehyde.

As inert solvents may be used, for instance: trichloroethane, tetrachloroethane, trichloroethylene, perchloroethylene, toluene, chlorobenzene, dichlorobenzene, diphenylmethane, chloronaphthalene or the final product. Preferred solvent is the final product. For that specific case it is useful to perform the phosgenation first without adding the final product. The final product may be added as solvent after the free hydroxyl group or groups have substantially been reacted and are no longer present as such, i.e. after decrease of the phosgene absorption or the release of HCl.

As acid halides having the formula III those are preferred wherein X represents chlorine or bromine, i.e. phosgene, oxalyl chloride, bromophosgene and oxalyl bromide. The use of phosgene is most advantageous. The process is carried through as described in German Offenlegungsschrift No. 2129584. Compounds which contain at least one tertiary or quatenary nitrogen or phosphorus atom, are used as catalysts, i.e. compounds in which N or P are bound to carbon by 3 or 4 valencies, two of these valencies being able to form a double bond.

Compounds of this kind have the general formula

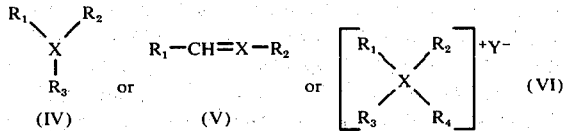
(IV)    (V)    (VI)

wherein X represents a nitrogen atom or a phosphorus atom, Y represents an inorganic or organic acid radical such as for example halogen⁻-ion, the $SO_4^{--}$-ion or the ion of an organic sulfonic acid, such as for example $CH_3OSO_3^-$ or $C_6H_5SO_3^-$ and $R_1$, $R_2$, $R_3$ and $R_4$ represent identical or different organic radicals such as straight-chain or branched alkyl groups having from 1–20, preferably from 1–12, especially from 1–4 carbon atoms, alkenyl groups, having from 2–20, preferably from 2–12, particularly from 2–4 carbon atoms, cycloalkyl groups having from 4–8, preferably from 4–6 carbon atoms, or phenyl groups or benzyl groups, or acyl groups having from 1–4 carbon atoms, preferably 1 or 2 carbon atoms, all the radicals R themselves may be substituted, preferably mono-substituted, by halogen, preferably by chlorine and/or bromine or by an alkoxy group having from 1–4 carbon atoms, preferably 1 or 2 carbon atoms, or by a dialkylamino group with alkyl groups having from 1–4 carbon atoms. Two of the radicals $R_1$ – $R_4$ may also form a ring such as is the case in N-methylpyrrolidone, pyridine, or 1-methylphospholene. The molecular weight of the catalyst used is preferably up to 500, especially up to 200.

Furthermore, it is possible to use nitrogen- or phosphorus-containing compounds of the general formula VII

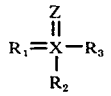

(VII)

wherein three of the nitrogen or phosphorus valencies are bound to carbon and wherein Z represents oxygen or, if X is phosphorus, also sulfur, two halogen atoms, especially 2 chlorine atoms, or the group $NR_5$, $R_5$ being $= R_1$ or H. It is also possible, as previously mentioned, that two or three of the radicals $R_1$ to $R_3$ form a cyclic system, optionally a heterocyclic system including a hetero-atom such as oxygen, sulfur or nitrogen.

Finally, there may also be used as catalysts the amides of different organic or inorganic monobasic dibasic or tribasic acids of tri- or pentavalent phosphorus. These catalysts are peramidated, contain two aliphatic radicals with up to 20 carbon atoms at each of the nitrogen atom(s), preferably alkyl groups having from 1–4 carbon atoms and carry as organic radicals on the phosphorus atom an aliphatic group having up to 20 carbon atoms, preferably an alkyl group with from 1–4 or a cycloalkyl group having from 4-8 carbon atoms or a phenyl or benzyl group, this radical optionally being also substituted, preferably by lower alkyl or alkoxy groups or by halogen.

The following compounds may therefore be used as catalysts:

A. Tertiary aliphatic and aromatic amines and phosphines such as trimethylamine, tripropylamine, tributylamine, triphenylamine, trimethylphosphine, triethylphosphine, tripropylphosphine, tributylphosphine, triphenylphosphine and tris-(p-dimethylaminophenyl)-phosphine and the corresponding mixed amines, phosphines, phospholanes and phospholenes as dimethylethylamine, diethylbutylamine, N-dimethylaniline, 4-methyl-N-dimethylaniline, diethylaniline, N,N-tetramethylphenylenediamine, or N-methylpyrrolidine; methyldiethylphosphine, dimethylpropylphosphine, diethylbenzylphosphine, 1-methylphospholene-3 and 1-ethyl-3-methyl-phospholene-3.

B. Azomethines such as hydrobenzamid, benzylidene-analine, o-, m-, p-methyl-, o-, m-, p-methoxy-, o-, m-, p-chlorobenzylidene-aniline, as well as corresponding derivatives of substituted anilines such as of o-, m- or p-toluidine, of o-, m- or p-nitroaniline, of o- and p-anisidine, as well as of o-, m- and p-chloroaniline.

C. quaternary ammonium salts or phosphonium salts such as tetramethylammonium chloride or -bromide, tetraethylphosphoniumchloride, trimethylbenzylammonium chloride, triethylbenzylammonium chloride, triethylbenzylammonium bromide, trimethylbenzylphosphonium chloride, triphenylethylphosphonium-2,4-diaminobenzene sulfonate.

D. Heterocyclic compounds displaying aromatic characteristics, such as pyridine, quinoline, their different derivatives such as alkyl and dialkyl derivatives, preferably methyl or dimethyl derivatives, imidazole, N-vinyl-imidazole, benzthiazole, 2-amino-6-ethoxybenzthiazole, and phosphabenzenes.

E. Acid amides such as dimethyl formamide, diethyl formamide, N-dimethylacetamide, N-diethylpropionamide, N-dimethylbenzamide, N-methyl-pyrrolidone, N,N'-tetramethyl-terephthalic acid amide, or ureas such as tetramethyl-urea and trimethylphenyl-urea.

F. Other nitrogen or phosphorus compounds having one N-atom or P-atom with a valency superior to 3 such as pyridine-N-oxide, trimethylphosphine oxide, tributylphosphine oxide, trihexylphosphine oxide, triphenylphosphine oxide, trihexylphosphine sulfide, triphenylphosphine sulfide, dimethylphenylphosphine oxide, dimethylphenylphosphine sulfide, dimethylchloromethylphosphine oxide, dimethyleicosylphosphine oxide, dimethyldodecylphosphine oxide, dimethylphosphine oxide, dimethylpyrrolidine-1-methyl-phosphine oxide, triphenyl-phosphine dichloride, dimethyldodecylphosphine sulfide, triphenylphosphine imine, dimethylchloromethylphosphine dichloride, N-2-dimethylphosphinyl-ethylmethylacetamide, N-2-dimethylphosphinylethylmethylamine, phospholene oxides such as 1-methylphospholene-1-oxide and 1-ethyl-3-methylphospholene-1-oxide.

G. Amides of phophinous acid and phosphonous acids and of phosphinic and phosphonic acids and of their thio-analogs such as ethanephosphonic acid bis-diethylamide, methanebutanephosphonous acid-dimethylamide, diethylphosphonous acid eisobutylamide, furthermore triamides of phosphoric acid and of thiophosphoric acid such as hexamethylphosphoric acid triamide.

All the catalysts are used in quantities from 0.001 to 5 % by weight or more, calculated on the phosphonic acid derivative used, preferably, in quantities from 0.5–2 % by weight. They may be used as such or in form of their salts, particularly as hydrochlorides.

The process is carried through preferably at temperatures between +65° and 200°C. Higher temperatures are sometimes possible. Especially preferred reaction temperatures are those between +100° and +180°C.

The reaction may be performed under pressure, for example at 5 to 10 atm. gauge or, if the process is performed without intermediate decompression also at the higher pressures generated by the formation of $CO_2$ (CO).

The reaction time may vary according to the temperature and the processing equipment, but generally it is from about 5 to 25 hours.

An excess of acid halide over the stoichiometric quantity is not essential, however, it may be useful to add such an excess for reducing the reaction time. In that case the most advantageous method is to have the excess acid halide consumed by fresh initial product upon leaving the reaction zone together with the waste gas, a column with counter current flow being most useful for that purpose. The whole process may also be performed continuously in known manner, expecially in a column or an equivalent device.

The reaction is performed preferably in such a way that the acid halide is added to the mixture of phosphonic acid derivative and catalyst, and the waste products (alkyl halide or alkali metal halide and $CO_2$ or CO) are eliminated from the reaction zone is known manner, if possible while the reaction is still going on, for example by distillation and/or fractioned condensation.

In certain cases it is preferred to add the catalyst in a later phase or towards the end of the reaction.

Vigorous stirring of the reaction mixture is advantageous, especially if gaseous acid halides such as phosgene are used. After the termination of the reaction, the reaction product is isolated by distillation.

The halogenomethane-phosphonic acid dihalides prepared according to the process of the invention are valuable intermediary products for the preparation of pesticides and flame retardants. For example, the reaction with glycine yields valuable herbicidal agents.

The process according to the present invention offers important technological advantages due to its simple practicability and especially by the fact that the waste products are gaseous or distillable and thus can be easily separated from the reaction products. The $CO_2$ formed in the course of the process can easily be purified to such an extent that it may escape into the atmosphere without pollution of the environment.

Generally, the catalyst used for the reaction remains as a residue upon distillation of the phosphonic acid halide and can be re-used for further reactions.

The following Examples illustrate the invention:

EXAMPLE 1

91 g (0.54 mole) of hydroxymethane-phosphonic acid diethylester and 1 g of pyridine are heated to 160°C. For 15 hours phosgene is added while stirring vigorously. Then 45 g chloromethane-phosphonic acid dichloride and 2 g of pyridine are added and at 160°C more phosgene is added for another 7 hours while stirring again vigorously. Then the excess phosgene is eliminated from the batch by means of nitrogen and the mixture is fraction-distilled.

115 g of chloromethane-phosphonic acid dichloride, $bp_{24}$: 96°–98°C (Lit.: $bp_{18}$: 90°–93°C) are obtained, representing a yield of 77.5 percent of the theory.

EXAMPLE 2

50 g (0.447 mole) of hydroxymethane-phosphonic acid are mixed with 1 g of pyridine and heated to 170°C. Now phosgene is added in a slow, continuous flow for 15 hours at 170°C, while stirring vigorously. Then are added 50 g of chloromethane-phosphonic acid dichloride and 1 g of pyridine, and more phosgene is then added for another 5 hours at 130°C, while stirring vigorously. Then the excess phosgene is eliminated by means of nitrogen and the mixture is distilled.

93 g of chloromethane-phosphonic acid dichloride are obtained, representing a yield of 86 percent of the theory.

EXAMPLE 3

185 g (1.0 mole) of crude hydroxymethane-phosphonic acid diethylester are mixed with 2 g of pyridine and heated to approx. 170°C. Phosgene is then introduced for 12 hours, while stirring vigorously. In course of this process the reaction mixture becomes very viscous. After cooling, another 4 g of pyridine are added and more phosgene is introduced at 170°C for another 7 hours. The work-up according to example 2 completed, 140.5 g of chloromethane-phosphonic acid dichloride are obtained, representing a yield of 78 percent of the theory.

What is claimed is:

1. A process for preparing halogenomethanephosphonic acid dihalides having the general formula

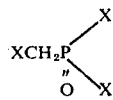

wherein X represents chlorine or bromine which comprises: reacting a member of the group consisting of hydroxymethane-phosphonic acid of the formula

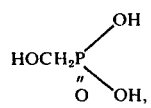

alkali metal or ammonium salts of hydroxymethane-phosphonic acid and mono- or di- alkyl esters of hydroxymethane phosphonic acid or alkali metal or ammonium salts of such esters, with acid halides having the formula

wherein $n$ is 1 or 2, in the presence of
1. compounds containing at least one 3- to 5-valent nitrogen or phosphorus atom, which is bound with at least 3 valences to organic radicals having up to 20 carbon atoms, two of said valences being able to form a double bond, or in presence of
2. fully amidated tribasic organic or inorganic acids of 3-valent or 5-valent phosphorus, the nitrogen-atoms of which are substituted by aliphatic radicals having up to 20 carbon atoms and the organic radicals of which may contain up to 20 carbon atoms.

2. A process as recited in claim 1 conducted in the presence of an inert solvent.

* * * * *